US006890349B2

(12) United States Patent
McGuckin, Jr. et al.

(10) Patent No.: US 6,890,349 B2
(45) Date of Patent: May 10, 2005

(54) COVERED STENT WITH SIDE BRANCH

(75) Inventors: James F. McGuckin, Jr., Radnor, PA (US); Peter W. J. Hinchliffe, Downington, PA (US)

(73) Assignee: Rex Medical, L.P., Conshohocken, PA (US)

( * ) Notice: Subject to any disclaimer, the term of this patent is extended or adjusted under 35 U.S.C. 154(b) by 213 days.

(21) Appl. No.: 09/973,365

(22) Filed: Oct. 9, 2001

(65) Prior Publication Data

US 2002/0052648 A1 May 2, 2002

Related U.S. Application Data

(60) Provisional application No. 60/240,009, filed on Oct. 13, 2000, and provisional application No. 60/278,361, filed on Mar. 23, 2001.

(51) Int. Cl.[7] .................................................. A61F 2/06
(52) U.S. Cl. ...................................... 623/1.13; 606/108
(58) Field of Search ............................... 623/1.12, 1.15, 623/1.35, 1.11, 1.13, 1.16; 606/198, 108, 191, 194–195

(56) References Cited

U.S. PATENT DOCUMENTS

| | | | |
|---|---|---|---|
| 4,512,338 A | | 4/1985 | Balko et al. |
| 4,994,071 A | * | 2/1991 | MacGregor .................. 606/194 |
| 5,342,387 A | * | 8/1994 | Summers ..................... 606/198 |
| 5,632,771 A | * | 5/1997 | Boatman et al. ........... 623/1.15 |
| 5,643,339 A | * | 7/1997 | Kavteladze et al. ....... 623/1.22 |
| 5,669,924 A | * | 9/1997 | Shaknovich ............... 623/1.11 |
| 5,749,825 A | | 5/1998 | Fischell et al. |
| 5,906,640 A | * | 5/1999 | Penn et al. ................. 623/1.15 |
| 5,961,548 A | | 10/1999 | Shmulewitz |
| 5,972,017 A | | 10/1999 | Berg et al. |
| 6,030,414 A | | 2/2000 | Taheri |
| 6,056,775 A | | 5/2000 | Borghi et al. |
| 6,156,063 A | | 12/2000 | Douglas |
| 6,210,429 B1 | | 4/2001 | Vardi et al. |
| 6,210,433 B1 | * | 4/2001 | Larre ........................ 623/1.15 |
| 6,264,682 B1 | * | 7/2001 | Wilson et al. ............. 623/1.11 |
| 6,409,750 B1 | * | 6/2002 | Hyodoh et al. ............. 623/1.1 |
| 6,514,281 B1 | * | 2/2003 | Blaeser et al. ............. 623/1.12 |
| 6,520,988 B1 | | 2/2003 | Colombo et al. |

FOREIGN PATENT DOCUMENTS

| | | |
|---|---|---|
| EP | 0792627 | 9/1997 |
| EP | 1029517 | 8/2000 |
| WO | WO 9745073 | 12/1997 |
| WO | WO 99/34749 | 7/1999 |
| WO | WO 9936002 | 7/1999 |

* cited by examiner

*Primary Examiner*—Julian W. Woo
*Assistant Examiner*—Nguyen Victor
(74) *Attorney, Agent, or Firm*—Neil D. Gershon

(57) ABSTRACT

A system for treating stenosis in a target blood vessel, such as the common carotid artery, comprising a graft portion having a main portion and a branch portion extending therefrom. The branch portion extends from the intermediate portion of the main portion at an angle thereto and is in fluid communication with the main portion. A first stent is associated with the main portion and is expandable from a first configuration to a second configuration to retain the main portion in position within the target vessel. A second stent is associated with the branch portion and is expandable from a first configuration to a second configuration to retain the branch portion in position within a branching vessel. In one embodiment, the branch portion is integral with the main portion. In an alternate embodiment the branch portion is connected to the main portion.

14 Claims, 11 Drawing Sheets

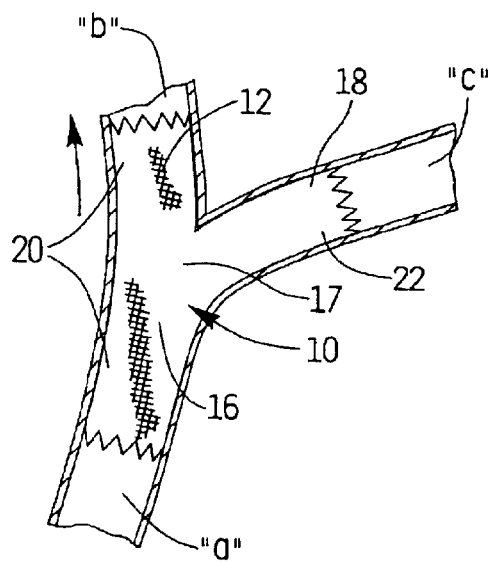
FIG_1A
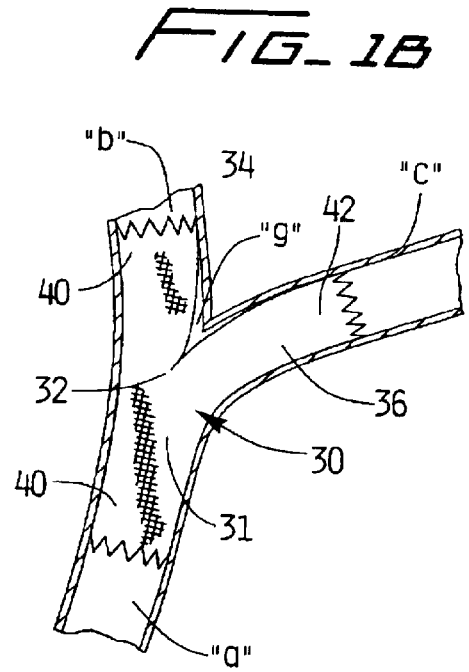
FIG_1B
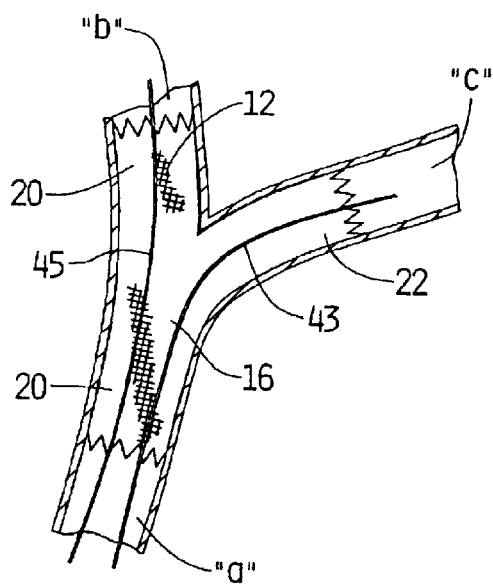
FIG_1C
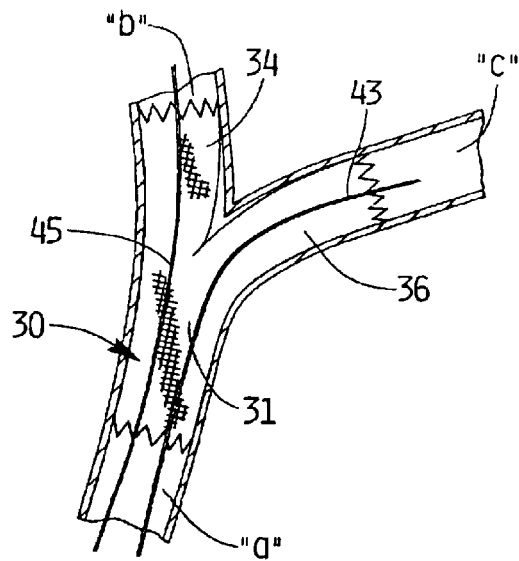
FIG_1D

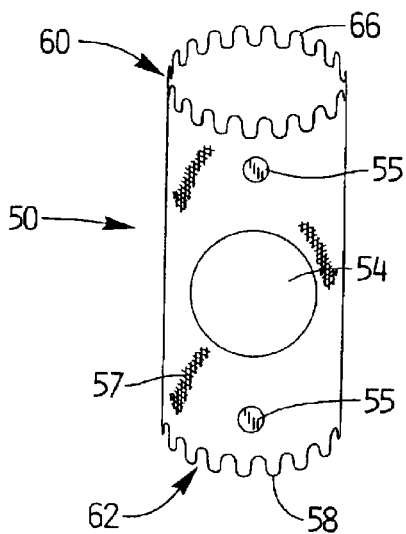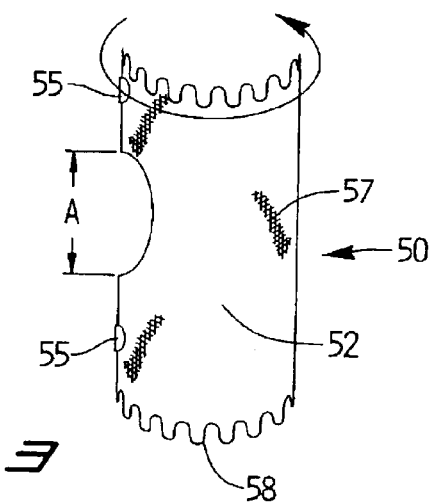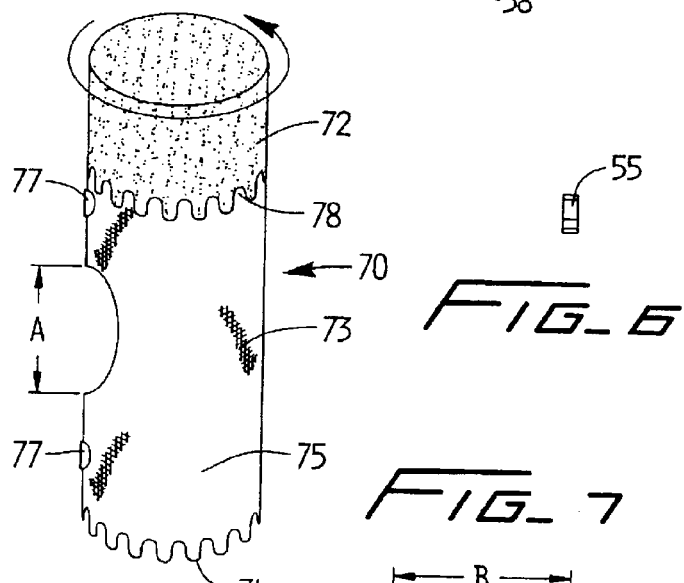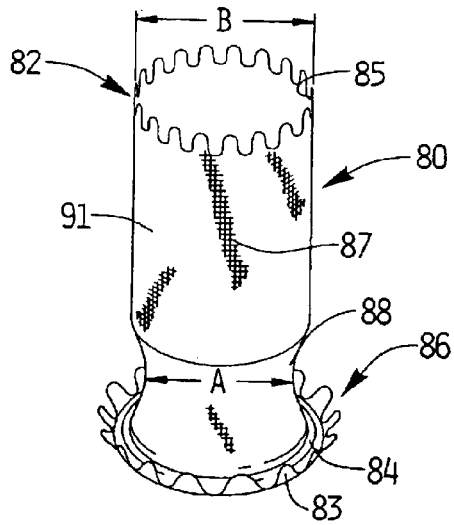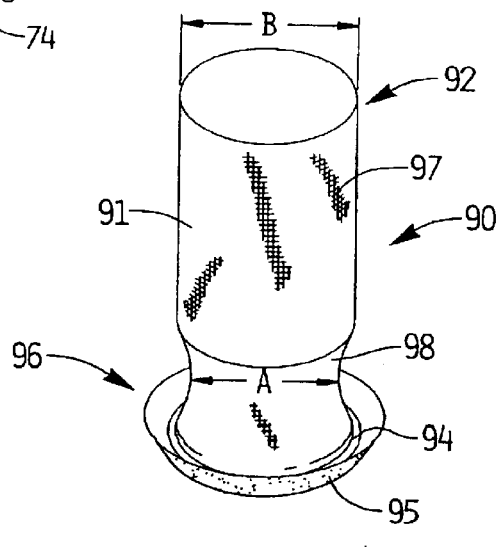

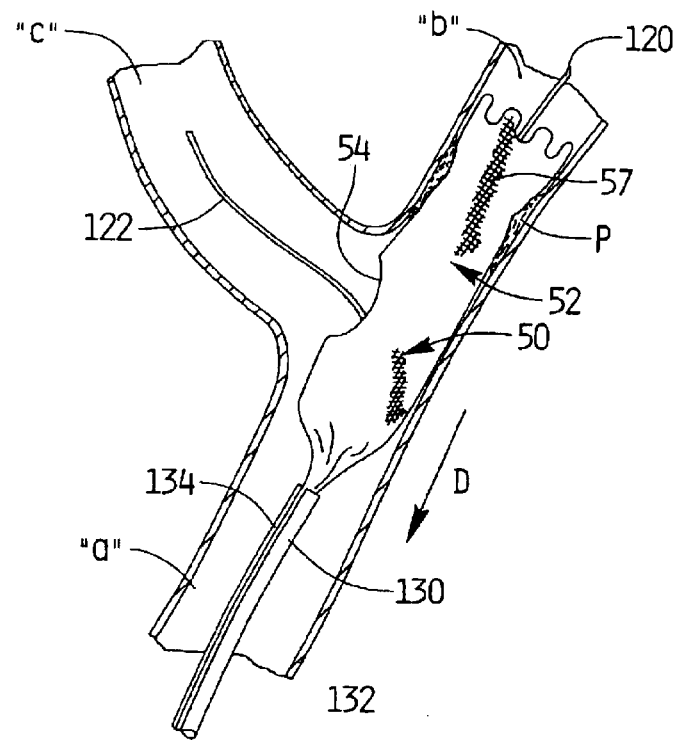
FIG_9A
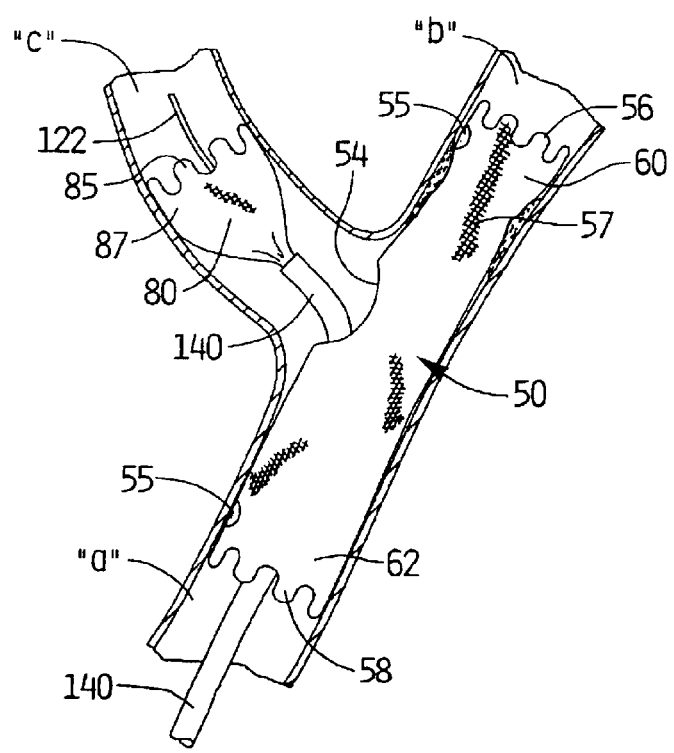
FIG_9B

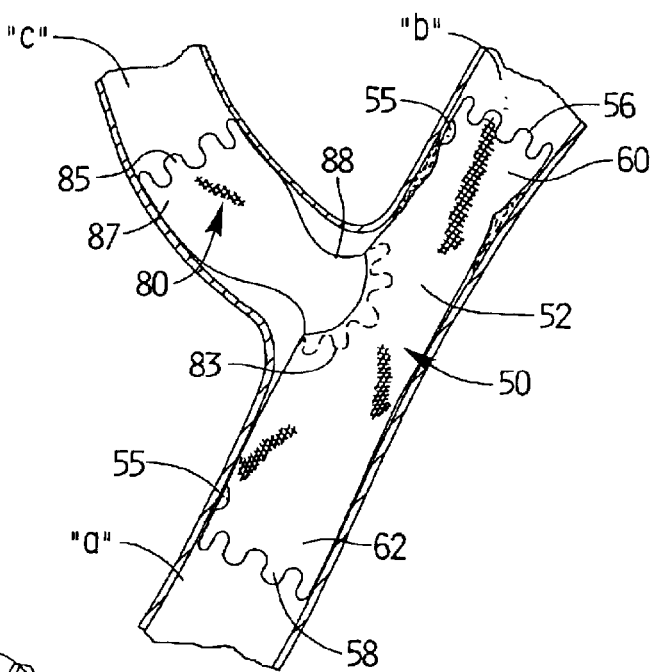
FIG_9C
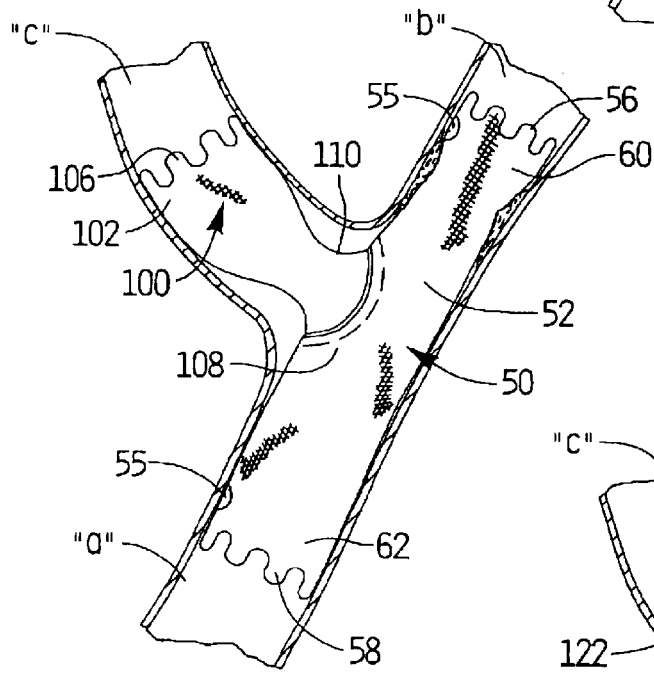
FIG_10
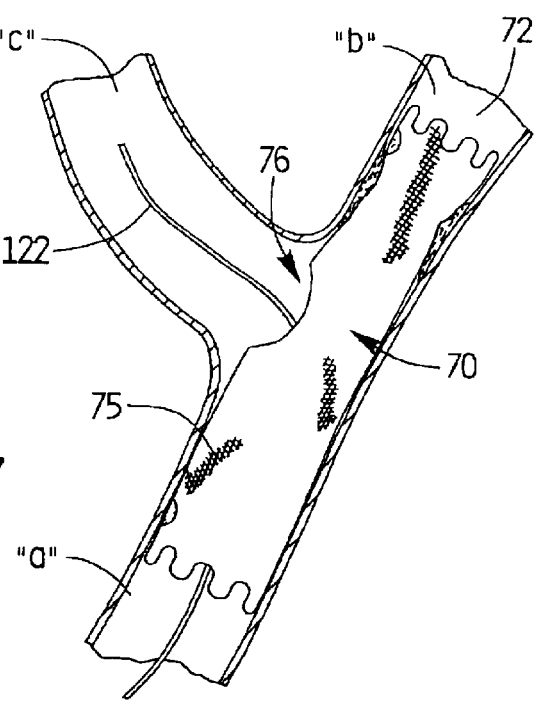
FIG_11

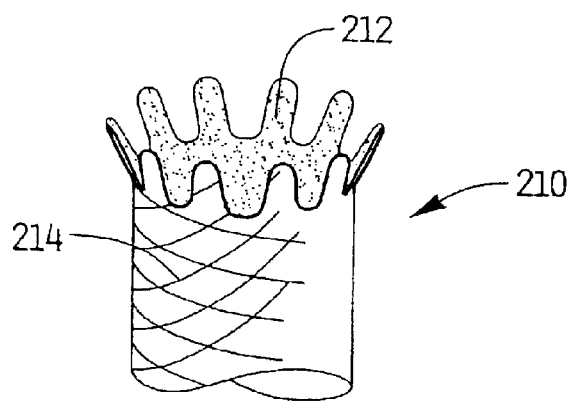
FIG_12A
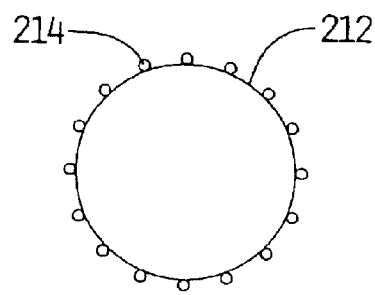
FIG_12B
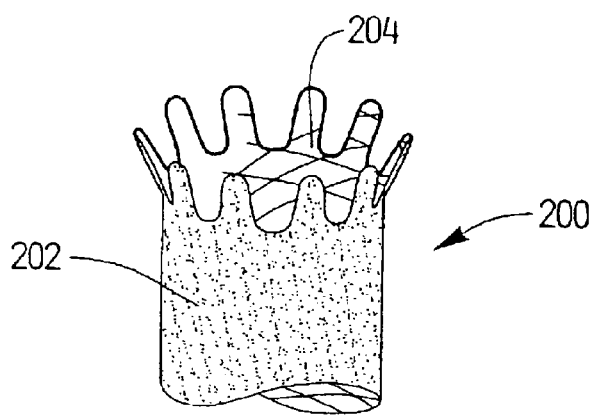
FIG_13A
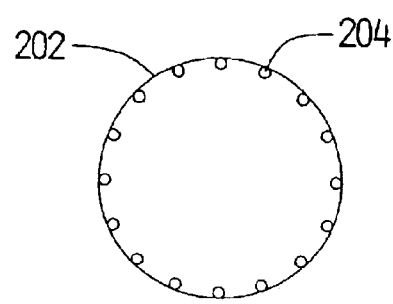
FIG_13B
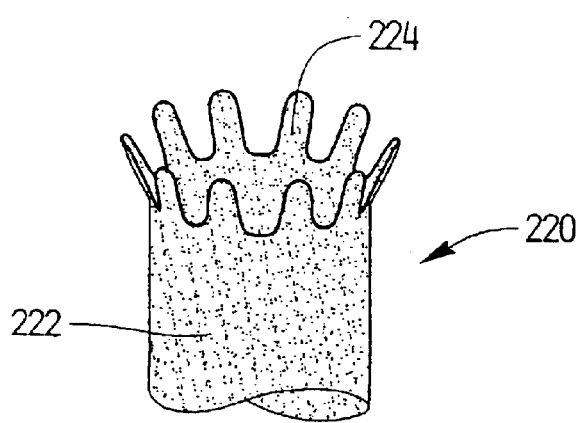
FIG_14A
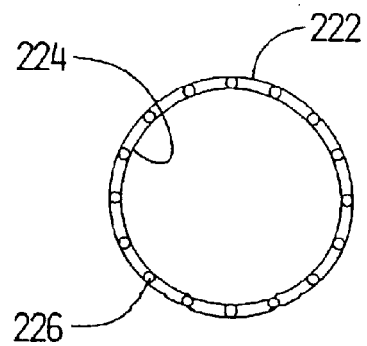
FIG_14B

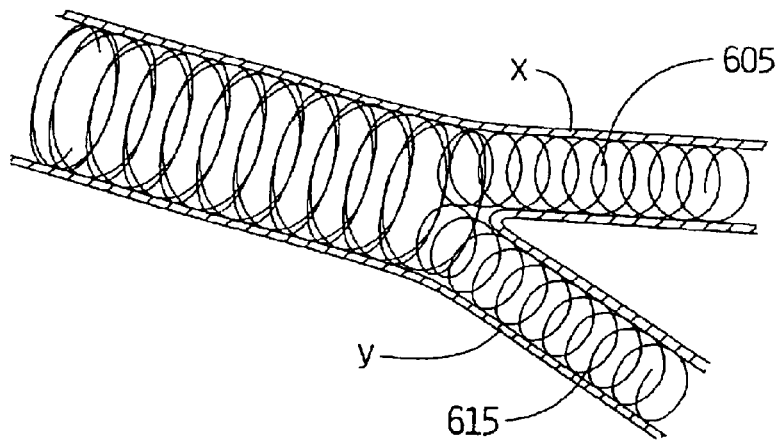
FIG_16
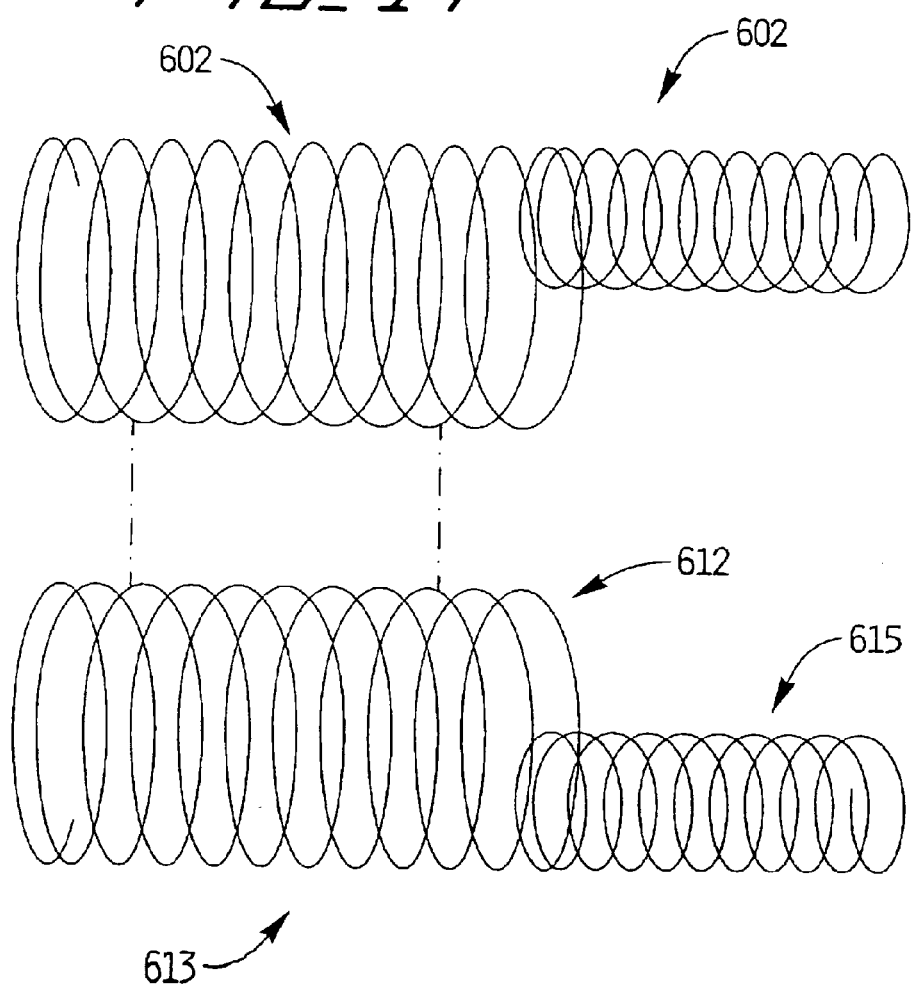
FIG_17

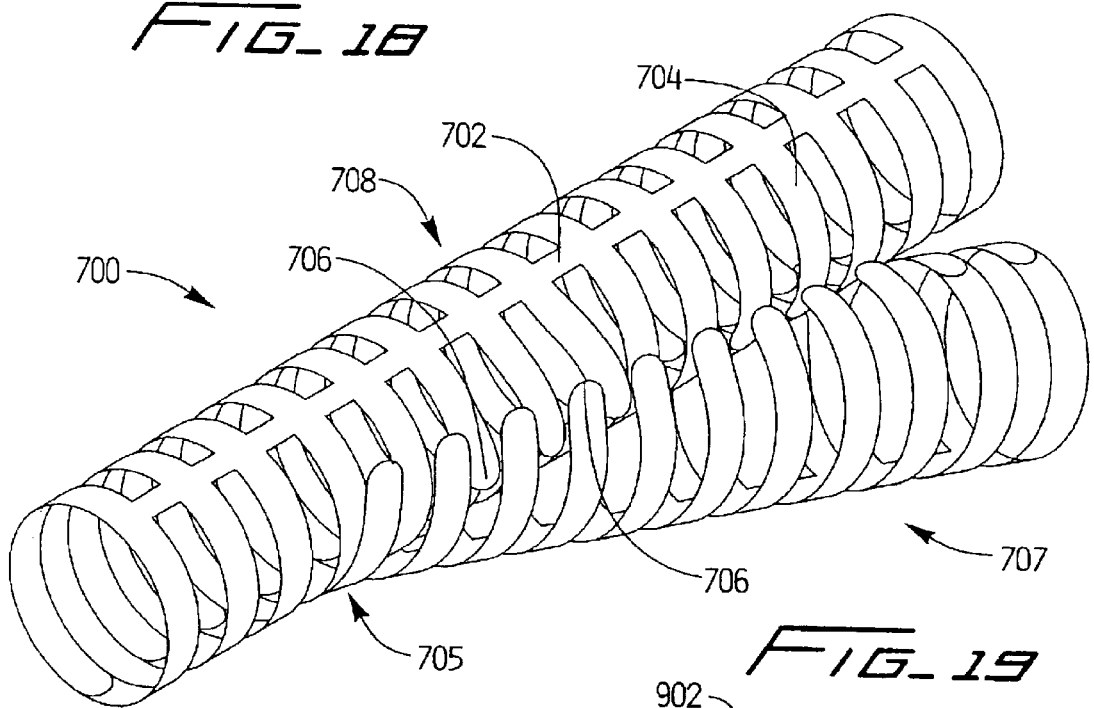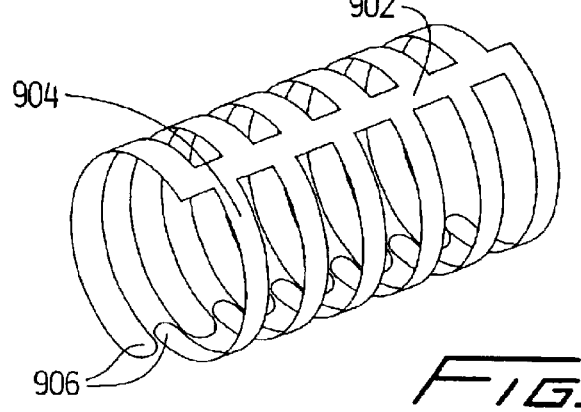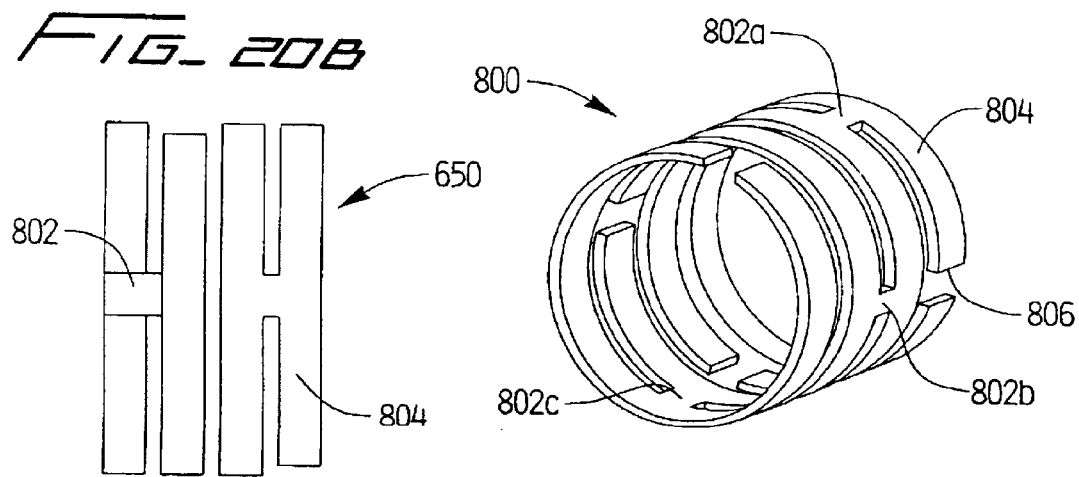

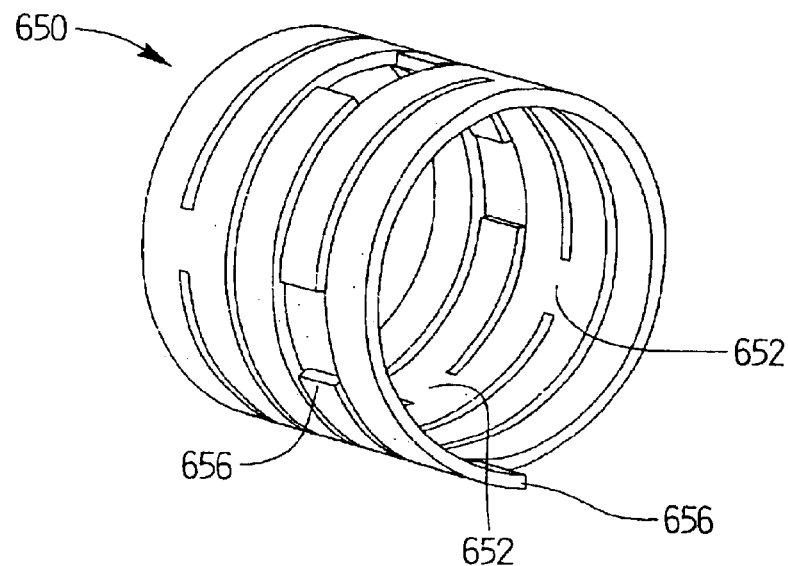
FIG_21A
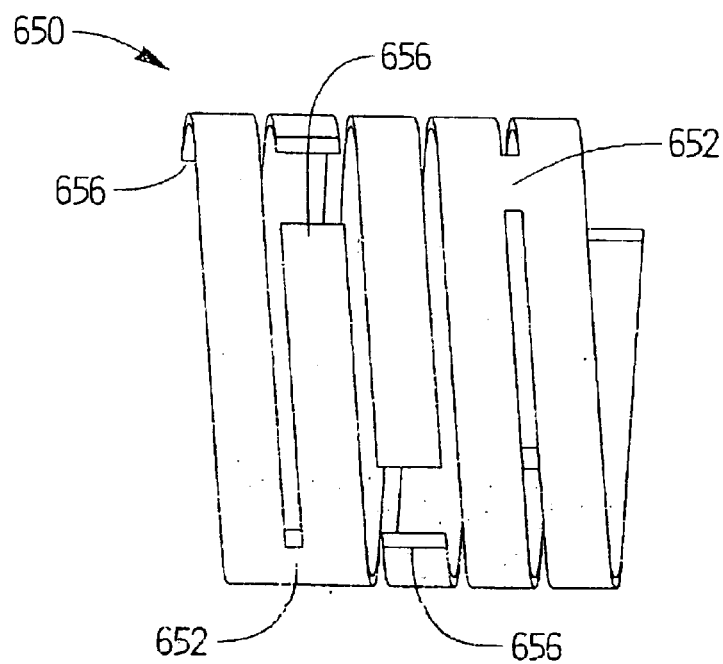
FIG_21B

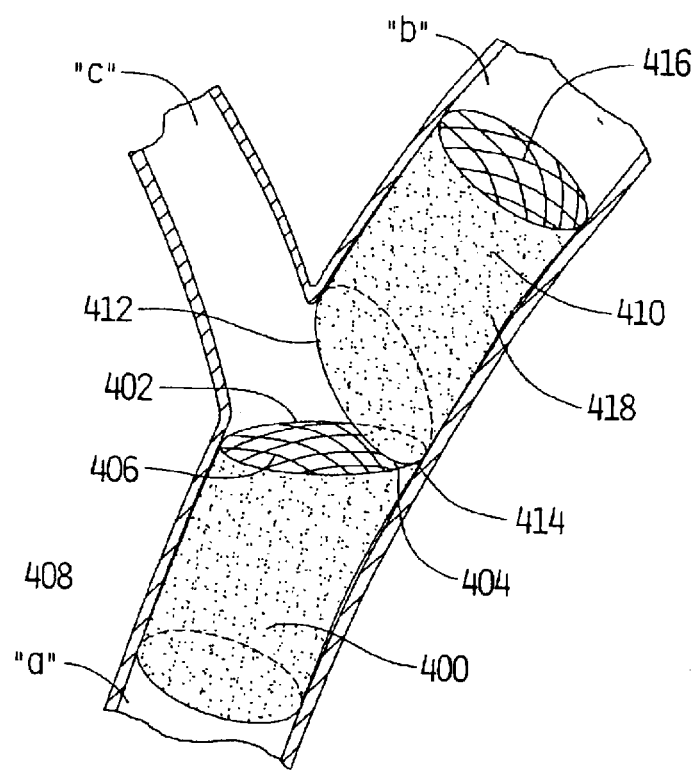
FIG_22
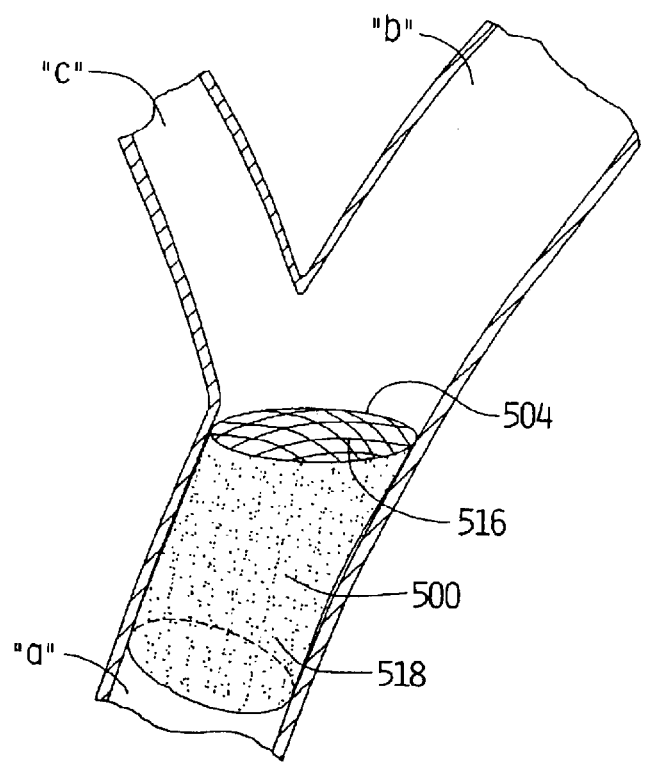
FIG_23

COVERED STENT WITH SIDE BRANCH

This application claims priority from provisional patent application Ser. No. 60/240,009, filed Oct. 13, 2000 and provisional patent application Ser. No. 60/278,361, filed Mar. 23, 2001, the entire contents of both applications incorporated herein by reference.

BACKGROUND

1. Technical Field

This application relates to a vascular stent and graft and more particularly to a covered stent having a side branch to accommodate a branching vessel.

2. Background of Related Art

The vascular disease of arteriosclerosis, also referred to as hardening of the arteries, is caused when fatty substances and plaque build up inside the artery walls over time and reduce the size of the arterial lumen (passageway), thereby restricting proper blood flow through the artery. This buildup which causes restriction of the vessel is called stenosis.

The right and left common carotid arteries arise from the aorta and are the principal blood supply to the head and neck. Each of the two common arteries divides to form external and internal carotid arteries to supply the blood to the head and neck. Arteriosclerosis of the carotid arteries if left untreated, will constrict the arterial passageway to such an extent as to prevent adequate supply of blood to the brain or ultimately will fully occlude the artery to cut off blood flow entirely, causing a stroke resulting in paralysis or even death.

Several methods are currently being utilized to treat arteriosclerosis of the carotid arteries. One method is an invasive surgical procedure where the vessel wall is cut open and the portion containing the plaque is removed. This procedure is traumatic, complex, and requires a long recovery time for the patient. It also results in weakening of the vessel wall since a portion of the wall is removed. A weakened wall can potentially result in an aneurysm which is a dilatation (expansion) of the artery, which adversely affects vessel function and if not surgically treated could be life threatening to the patient.

With the advent of minimally invasive procedures, and particularly intraluminal (within the vessel) procedures for many types of surgeries in order to reduce trauma to the patient, decrease morbidity, reduce the patient recovery time and reduce hospital costs, the industry has been attempting to develop ways to minimally invasively treat arteriosclerosis of the carotid arteries. Initially, balloon angioplasty, a procedure used for treating coronary arteries, was attempted. In angioplasty, a balloon is placed in the stenosed (restricted) portion or the vessel and inflated to fissure and compress the plaque against the vessel (arterial) wall, thereby increasing the opening in the vessel to improve blood flow. However, angioplasty of the carotid arteries was found to create grave risks because plaque, rather than just being compressed, could inadvertently be dislodged from the arterial wall and travel up through the internal carotid artery to the brain, causing a stroke.

To help maintain the enlarged opening created by an angioplasty balloon in coronary arteries, stenting has become widespread. Stenting involves the placement of a structural support (a stent), typically composed of metal, in the stenosed region either after balloon angioplasty is completed or in conjunction with the angioplasty. The stent is expanded in the vessel to provide a radial force against the vessel wall in an attempt to maintain the opening in the vessel created by the angioplasty balloon and overcome the elastic recoil which occurs after balloon angioplasty. Although stents may reduce the chance of dislodgement and flow of plaque to the brain, stents provide their own risks. For example, thrombus can build on the stent structure over time, which can eventually become dislodged and travel through the internal carotid arteries to the brain causing embolic stroke. Also, intimal hyperplasia (buildup of scar tissue) around the stent can occur, resulting in restenosis (re-constriction of the vessel) within or juxtaposed to the stent.

To avoid the flow of dislodged plaque or thrombotic material to the brain, covered stents have begun to be utilized in the common carotid arteries. The stents are covered with graft material, such as PTFE, and compressed against the vessel (arterial) wall, thereby sandwiching any dislodged plaque between the graft and vessel wall to prevent dislodgement. Thrombotic material can also be captured between the graft and wall. Although these covered stents reduce the dislodgement problem discussed above, the placement of the graft material can create other problems. If the covered stent is placed in a portion of the common carotid artery which does not have any vessels branching off, blood flow is maintained. However, problems can arise if the stenosis is adjacent to a branching vessel because implantation of the covered stent will require closing off or blood flow to the branching vessel as the graft material will extend past the branch opening. For example, if the graft of a covered stent is placed in the common carotid artery extending into the internal carotid artery, the graft will cover the juncture of the external carotid artery, thereby cutting off blood flow through the external carotid artery to the face and scalp and occluding potentially life saving collateral blood supply to the brain. Thus, although the problems associated with the stenosis in the common carotid artery might be alleviated by the covered stent, the patient may still have reduced blood flow because the external carotid artery will no longer be able to supply collateral blood to the brain if the stent were to fail. Since the overall blood flow is reduced, the likelihood of stroke will increase.

Additionally, by cutting off the opening to the external carotid artery, future access to this artery for treatment is prevented. Therefore, if an aneurysm or stenosis develops in this artery, the covered stent would prevent intraluminal access to the target region.

It would therefore be advantageous to provide a covered stent that could be used in the carotid arteries which would not adversely affect blood flow in branching vessels. Such covered stent would thereby advantageously enlarge the restriction (stenosis) in the common carotid artery to improve blood flow therethrough without disadvantageously reducing blood flow or restricting access to connecting arteries.

SUMMARY

The present invention overcomes the disadvantages and deficiencies of the prior art. The present invention provides a system for treating stenosis in a target blood vessel comprising a graft portion having a main portion and a branch portion extending therefrom. The branch portion extends from the intermediate portion of the main portion at an angle thereto and is in fluid communication with the main portion. A first stent is associated with the main portion and is expandable from a first configuration to a second configuration to retain the main portion in position within the target vessel. A second stent is associated with the branch portion and is expandable from a first configuration to a second configuration to retain the branch portion in position within a branching vessel.

In one embodiment, the branch portion is integral with the main portion. In an alternate embodiment the branch portion is connected to the main portion. In this embodiment, the intermediate portion has an opening therethrough and the branch portion preferably includes a flange at a proximal end having a diameter greater than a diameter of the opening to thereby retain the flange within the main portion. In another alternate embodiment, the main and branch portions are formed by a bifurcated graft.

The ends of the main graft portion and branch graft portion may have a plurality of petals to reduce the radial force against the vessel walls. The petals preferably flare out to a larger diameter than the other portions of the graft.

In one embodiment, the first and second stents are positioned within the main and branch portions, respectively, so the main and branch portions expand upon expansion of their respective stents. In another embodiment, the first and second stents overlie the main and branch graft portions.

In another embodiment, the main and branch portions include a longitudinally extending spine and a plurality of curved ribs extending from the spine. The ribs preferably terminate at first and second tips which interleave with first and second tips of adjacent ribs. In another embodiment, the main and branch portions include a series of spines spaced axially and radially with respect to each other.

The present invention also provides a stent for treating a stenosis in a target blood vessel comprising an expandable stent having an enlarged opening in the intermediate portion configured to allow unobstructed passage of blood into the main lumen of the stent. The opening is aligned with a vessel branching off the target vessel to maintain flow between the target vessel and the branching vessel. The stent may include a graft associated therewith having an opening aligned with the opening in the intermediate portion of the stent to allow passage of blood. The opening in the intermediate portion of the stent and the opening in the graft can be configured to receive a second graft therethrough so that the second graft extends outwardly through the openings at an angle to the first graft.

The present invention also provides a method of implanting first and second stents with associated grafts within first and second vessel portions extending at an angle with respect to each other. The method comprises inserting a first guidewire to guide a first stent with an associated first graft to a target region of a first vessel;

inserting a second guidewire to guide a second stent with an associated second graft to a second vessel branching from the first vessel;

inserting a delivery device containing the first stent with the associated first graft over the guidewire to the target vessel region;

removing the delivery device to enable the first stent with the associated first graft to expand against the wall of the target vessel;

inserting a second delivery device containing a second stent with the associated second graft over the second guidewire to the second vessel; and removing the delivery device to enable the second stent with the associated second graft to expand against the wall of the second vessel and fluidly communicate with the first stent and associated graft.

The present invention also provides a specific method of implanting first and second stents with associated first and second grafts within the carotid artery so the first graft extends from the common carotid artery into the internal carotid artery, past the juncture of the common carotid artery and the external carotid artery, and the second graft is positioned in the external carotid artery thereby maintaining flow between the common carotid artery and the external carotid artery.

BRIEF DESCRIPTION OF THE DRAWINGS

Preferred embodiment(s) of the present invention are described herein with reference to the drawings wherein:

FIG. 1A is a side view of a first embodiment of the covered stent of the present invention implanted in the right common and internal carotid arteries and having an integral branch extending into the right external carotid artery;

FIG. 1B is a side view of an alternate embodiment of the covered stent implanted in the right common and internal carotid arteries and having a bifurcation to branch into the right external carotid artery;

FIG. 1C illustrates the covered stent of FIG. 1A positioned over the first and second guidewires (the delivery sheath not shown for clarity);

FIG. 1D illustrates the covered stent of FIG. 1B positioned over the first and second guidewires (the delivery sheath not shown for clarity};

FIG. 2A is a perspective view of another embodiment of the covered main stent of the present invention having an opening in a sidewall to receive a covered branch stent therethrough;

FIG. 2B is a perspective view of the covered stent of FIG. 2 shown rotated to align the opening with the branching vessel;

FIG. 3 is a perspective view of yet another embodiment of the covered stent of the present invention having an opening in a sidewall to receive a covered branch stent and further having an unsupported extension;

FIG. 4 is a perspective view of a first embodiment of the covered branch stent insertable into the side opening of the covered stent of FIGS. 2 or 3 and having a flange with petals:

FIG. 5 is a front elevation view of the radiopaque disc positioned on the covered stent of FIGS. 2 and 3;

FIG. 6 is a side elevation view of the radiopaque disc of FIG. 5;

FIG. 7 is a perspective view of second embodiment of the covered branch stent of the present invention insertable into the side opening of the covered stent of FIGS. 2 or 3 and having smooth proximal and distal ends;

FIGS. 8–9 are side views illustrating delivery of the covered main stent and branch stent of FIGS. 2 and 4 within the left carotid arteries, wherein

FIG. 9A illustrates the delivery sheath for the covered main stent being withdrawn to place the covered main stent in the common and internal carotid arteries and further showing the second guidewire extending through the side opening;

FIG. 9B illustrates the delivery sheath for the covered main stent fully withdrawn to position the covered main stent in the common and internal carotid arteries and further showing the delivery sheath for the covered branch stent partially withdrawn to place the covered branch stent in the external carotid artery; and FIG. 9C illustrates the delivery sheath for the covered branch stent fully withdrawn from the body to position the covered branch stent of FIG. 4 in the external carotid artery;

FIG. 10 illustrates a covered branch stent having petals at its distal end and a smooth proximal end, positioned in the left external carotid artery and connected through the side opening to the covered main stent;

FIG. 11 illustrates the covered main stent of FIG. 3 positioned in the left common and internal carotid arteries with the second guidewire extending through the side opening for guiding the branch stent;

FIGS. 12A and 12B are perspective and cross sectional views, respectively, of a stent and graft arrangement of the present invention wherein the stent is positioned outside the graft;

FIGS. 13A and 13B are perspective and cross sectional views, respectively, of a stent and graft arrangement of the present invention wherein the stent is positioned inside the graft;

FIGS. 14A and 14B are perspective and cross sectional views, respectively, of a stent and graft arrangement of the present invention wherein the graft is positioned on both the inside and outside of the stent;

FIG. 16 is a side view of an alternate embodiment of the present invention illustrating a pair of coils utilized to accommodate a branching vessel;

FIG. 17 is an exploded view of the pair of coils of FIG. 16.

FIG. 18 is a perspective view of another alternate embodiment of the present invention illustrating a bifurcated stent, with overlapping ribs, to accommodate a branching vessel;

FIG. 19 is a perspective view of another alternate embodiment of the bifurcated stent having non-aligned interleaving ribs;

FIG. 20A is a perspective view of a segment of yet another alternate embodiment of the bifurcated stent having a staggered supporting spine to provide uniform rigidity;

FIG. 20B is a side view of the stent of FIG. 20A;

FIG. 21A is a perspective view of another alternate embodiment of the bifurcated stent having a helical configuration to form a spring-like element; and FIG. 21B is a side view of the stent of FIG. 21A;

FIG. 22 is a perspective view of an alternative approach to accommodate a branching vessel which utilizes, as shown, a pair of juxtaposed covered stents with angled adjacent ends to accommodate blood flow from a branching vessel; and FIG. 23 is a perspective view of an alternative approach to accommodate a branching vessel, similar to FIG. 22, except utilizing a single covered stent with an angled end to accommodate blood flow from a branching vessel.

DETAILED DESCRIPTION OF PREFERRED EMBODIMENTS

Figure 8A:
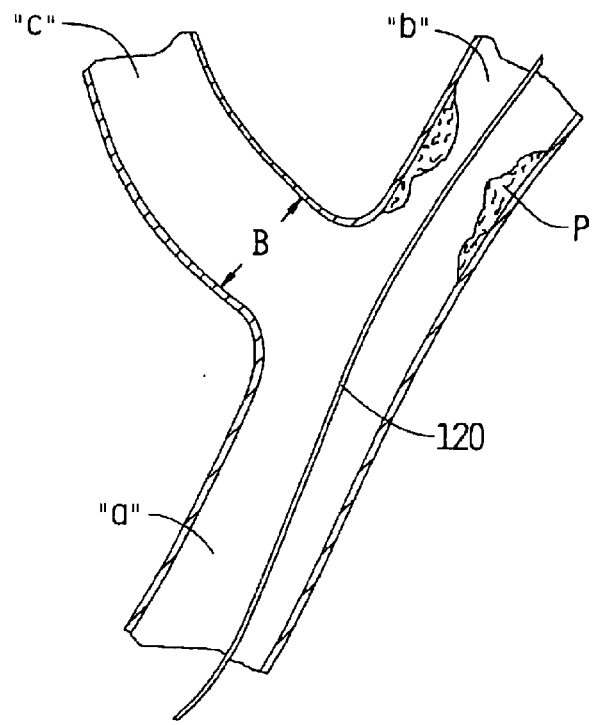
FIG. 8A illustrates a first guidewire inserted through the left common and internal carotid arteries past the region of stenosis.

Referring now in detail to the drawings wherein like reference numerals identify similar or like components throughout the several views, several embodiments of covered stents are illustrated to accommodate a branch of a target vessel. The covered stent includes a side branch, which can be either integral as shown in FIGS. 1A and 1B or a separate "branch" stent attached to a "main" stent as shown in FIGS. 2–4 and 7. The side branch extends into a vessel branching from the target vessel. The stent functions to expand the constricted passage, i.e. the stenosis, created by plaque buildup inside the vessel wall. A graft, composed of material such as PTFE or other known materials, is positioned over the stent (referred to as a "covered stent"), as shown in FIGS. 13A and 13B, so when the stent is expanded the graft is pushed against and retained against the inside vessel wall, thereby compressing the plaque, which might otherwise become dislodged, between the graft and the vessel wall. The stent retains the graft in place which creates a passageway for blood flow.

Currently, a covered stent having only a longitudinal directional component is placed inside the vessel wall. However, if the covered stent is placed adjacent a branching vessel, then that branching vessel will be closed off, preventing blood flow therethrough. For example, if in treating stenosis in the common carotid artery, a covered stent is placed in the common carotid artery extending to the internal carotid artery, the graft will extend past the juncture of the external carotid artery, thereby undesirably blocking blood flow to the external carotid artery. The covered stent of the present invention has an angled side branch which extends into the branching vessel, e.g. the external carotid artery, thereby allowing blood flow through the branching vessel which would otherwise be blocked if an elongated covered stent was placed in the artery across the juncture.

The covered stent of the present invention is described herein for use in carotid arteries by way of example. However, it should be understood that it is contemplated that the stent can be utilized in other vessels such as the coronary arteries, the descending aorta and renal arteries, the external iliac and internal iliac arteries and the common femoral and deep femoral arteries. Thus, the covered stent of the present invention, as can be appreciated, has application for vessels where a stenosis is adjacent a branching vessel. The covered stent of the present invention can also be utilized for other vascular procedures where it would extend past the juncture of the target vessel and a branching vessel.

With reference now to FIGS. 1A–1D, and with reference to use in the carotid arteries by way of example, two embodiments of the covered stent of the present invention having an integral side branch are disclosed. In the first embodiment, shown in FIG. 1A, covered stent 10 includes a graft 12 and an underlying main stent 20 and branch stent 22, only partially and schematically shown for clarity. Graft 12 includes a main portion 16 and a side branch portion 18 integral therewith. Main stent 20 underlies main graft portion 16 and branch stent 22 underlies side branch graft portion 18. Side branch portion 18 extends from an intermediate portion 17 of the covered stent 10 as shown. The branch portion 18 ensures that blood can continue to flow through the right external carotid artery "c", in the direction of the arrows, once the graft portions 16, 18 and underlying stents are positioned in the right common carotid artery "a", right internal carotid artery "b", and right external carotid artery "c".

FIG. 1B illustrates an alternate embodiment of the covered stent having an integral branch portion. Covered stent 30 includes a graft 31 bifurcated at its distal end portion 32 to form a first or main graft leg 34 and a second or side (branch) graft leg 36. Stent 40 underlies main leg 34 and stent 42 underlies side leg 36. Like covered stent 10, covered stent 30 is shown positioned to treat a stenosis in the right common carotid artery "a" with the main leg 34 extending into the internal carotid artery "b" and the side leg 36 extending into the right external carotid artery "c". It should be appreciated that the bifurcated covered stent 30 of FIG. 1B is more versatile in that it can accommodate various anatomies. The presence of gap "g" adjacent the bifurcation does not affect the desired blood flow.

Grafts 12 and 31 have petals at their ends as shown, the function of which is described below in conjunction with alternate embodiments.

Covered stents 10 and 30 are inserted in similar manners with FIG. 1C depicting insertion of covered stent 10 and FIG. 1D depicting insertion of covered stent 30. Two separate guidewires 43, 45 are inserted intraluminally, one extending through the right common carotid artery "a" into the internal carotid artery "b" and the other extending through the right common carotid artery into the external carotid artery "c". The covered stent 10 or 30 has its respective side branch graft portion 18 or side graft leg 36 folded towards the main graft portion 16 or main graft leg 34. The covered stent with the folded branch is then placed in a delivery catheter or sheath (not shown) with the stents positioned over the respective guidewires. The delivery catheter is advanced intraluminally to the target region, and then withdrawn, allowing the branch portion 18 or side leg 36 to unfold into the external carotid artery "c" and the respective stents 20,22 and 40,42 to expand to a larger diameter configuration. In the larger configuration, the stents apply a radial force against the vessel wall, thereby retaining the graft 12 or 31 against the vessel wall. As can be appreciated, blood can continue to flow through the graft from the common carotid artery through the external carotid artery FIGS. 2–7 illustrate a different approach for accommodating the vessel branch. Instead of an integral branch as in FIGS. 1A and 1B, a separate covered stent branch is attached, preferably in situ, to the covered main stent. More specifically, and initially with reference to FIG. 2A, a covered main stent 50 is illustrated comprising a graft 52 and an underlying stent 57. It should be noted that in FIGS. 1–11, the stent is shown schematically and only partially for the sake of clarity. In all embodiments, the underlying stent can extend the length of the graft or only along part or its length. Also, more than one stent can be utilized to retain the main graft portion and to retain the branch graft portion. Additionally, the stent can be composed of metallic or polymeric material, and include an opening in an intermediate portion to align with the opening in the graft as described below.

Referring back to FIG. 2A, graft 52 includes an opening 54 in its sidewall, in an intermediate portion, to accommodate a branch stent described below. Radiopaque discs or markers 55 are positioned adjacent the side opening 54 to facilitate locating the opening 54 during surgery to in turn facilitate attachment of the branch stent. Although disc shaped, other shaped radiopaque markers or other indicators at various locations can be used to facilitate proper orientation of the opening 54. Leaflets or petals 56, 58 are positioned on the distal and proximal end portions 60, 62, respectively, of graft 52 to reduce stress on the vessel wall by reducing the radial force against the wall. FIG. 2B illustrates how the covered stent 50 can be rotated to orient the side opening 54 towards the branching vessel. Side opening 54 has a diameter "A" dimensioned to receive a branch stent as discussed below. The stent 57 also includes an opening, such as that shown in FIG. 15, which aligns with the side opening 54 in graft 52 to ensure blood flow therethrough.

FIG. 3 illustrates an alternate embodiment of the covered main stent, designated by reference numeral 70. Covered stent 70 is similar to stent 50 in that it has an underlying metallic stent 75 and a graft 73 having a radiopaque indicator discs 77, side opening 76 having diameter "A" to receive a branch stent, and petals 74, 78. However, covered stent 70 additionally has an extension 72 at a distal end, which is unsupported by stent 75. This unstented extension reduces the radial force against the vessel wall in that region and may also allow placement of a portion of the graft in a vessel region where stenting is ill advised. Stent 75 also includes an opening (not shown) in a sidewall to align with side opening 76 of graft 73.

A first embodiment of the independent covered branch stent, illustrated in FIG. 4, is designated by reference numeral 80 and has a graft 81 and underlying stent 87. Graft 81 has a first end portion 82, a flange 84 at a second end portion 86, and a waist or reduced diameter portion 88. Underlying stent 87 would similarly have a conforming narrowed portion or otherwise configured or designed so that upon expansion, graft 81 retains its waist 88. As indicated, waist 88 has an external diameter "A", equal to the diameter of the opening 54 or 76 in the sidewall of covered main stents 50 or 70. The flange 84 and the portion of the covered stent distal of the waist 88 have diameters larger than diameter "A" to ensure the covered branch stent 80 does not slip through or out of opening 54 or 76 in covered main stent 50 or 70, respectively. Petals or leaflets 83, 85 function to reduce the radial force as described above.

FIG. 7 illustrates an alternate embodiment of the covered branch stent having a graft 91 and underlying stent 97. Branch stent 90 has a flange 94 with a smooth portion 95 and a smooth distal end 92. Waist portion 98 has a diameter "A" less than diameter "B" and equal to the diameter "A" of the opening 54 or 76 of covered main stents 50 or 70. The larger diameter "B" and the larger diameter of the flange 94 ensure the branch stent 90 is retained within the covered main stent.

Figure 8B:
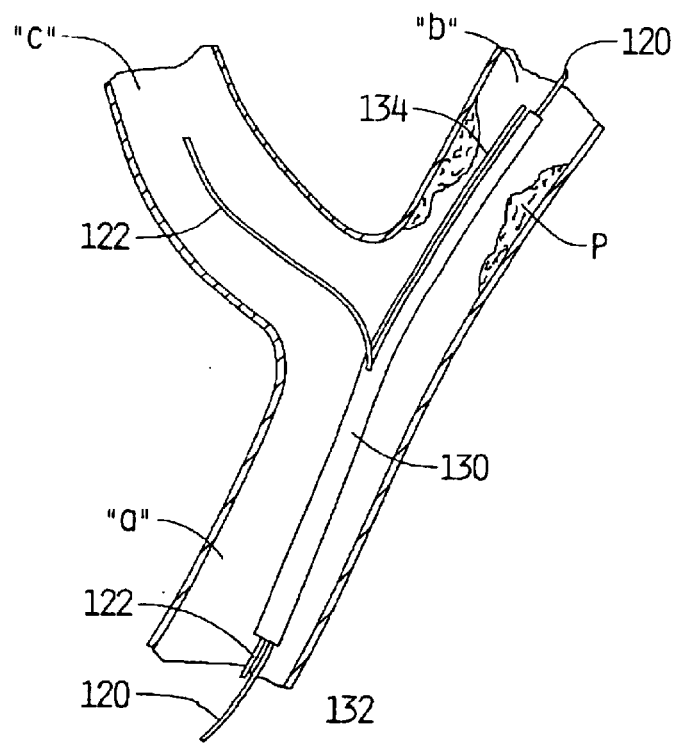
FIG. 8B illustrates the delivery sheath for the covered main stent positioned over the first guidewire in the left common and internal arteries and a second guidewire extending through the longitudinal slot in the sheath into the left external carotid artery.

The method of inserting the covered stent of the present invention in the left carotid arteries will now be described with reference to FIGS. 8A–9C. A first guidewire 120 is inserted through the common carotid artery, preferably through an entry point in the femoral artery, and extends to the internal carotid artery as shown in FIG. 8A, past the target region of stenosis having plaque "P". A second guidewire 122 extends through the common carotid artery into the external carotid artery. (An angioplasty balloon (not shown) is introduced over the guidewire 120 to pre-dilate the vessel). A delivery catheter or sheath 130 containing the covered main stent 50 of FIG. 2A therein, is threaded over the guidewire as shown in FIG. 8B, with the proximal end of the guidewire 120 extending beyond the proximal end 132 of the sheath 130. The main covered stent is thus positioned inside the sheath 130 and over the guidewire 122. Sheath 130 has a longitudinally extending slot 134, of sufficient size to accommodate a second guidewire 122. The slot 134 extends a sufficient distance proximally so at least a portion of the slot is in alignment with the external carotid artery "c" as shown. This allows withdrawal of the sheath 130 as described below. Once the sheath 130 is advanced into the internal carotid artery "b" so the covered stent 50 is aligned with the target vessel region, i.e. the portion of the vessel having the stenosis, the sheath 130 is withdrawn in the direction of arrow D in FIG. 9A, thereby allowing the stent 57 to expand to press the graft 52 against the vessel wall. The stent is preferably composed of shape memory material, such as Nitinol, that expands from a smaller configuration to its larger memorized configuration inside the body. As the sheath 130 is pulled proximally, the second guidewire 122 remains in place within the external carotid artery. The longitudinal slot 134 allows for this proximal movement without interfering with the guidewire 122.

Upon full withdrawal of the sheath 130, leaving the covered main stent 50 positioned as shown in FIG. 9B, the sheath 130 is removed from the patient, leaving the second guidewire 122 in place as shown. Note that with the visual aid (e.g. X-ray) of the radiopaque markers, the covered main stent 50 can be rotated, if necessary, to ensure alignment of the opening 54 with the lumen (passageway) of the branching external carotid artery "c".

A second delivery catheter or sheath 140, containing the covered branch stent 80 of FIG. 4 is then inserted over the second guidewire 122 and through the expanded covered main stent 50, exiting through opening 54 and into the branching vessel, e.g. the common carotid artery. (FIG. 9B) The sheath 140 is withdrawn proximally allowing the covered branch stent 80 to expand against the vessel wall. Note that only a portion of the covered branch stent 80 is advanced through the side opening 54, leaving the flanged proximal portion within the interior of the covered main stent 50, (see FIG. 9C) abutting the internal walls of the main stent 50 adjacent the side opening 54, to ensure the branch stent 80 does not become detached.

The sheath 140 is then fully withdrawn and removed from the body, allowing the stent 87 to expand and press the graft 81 against the wall of the external carotid artery as shown in FIG. 9C. (The stent 87 is also preferably composed of shape memory material and expands to its memorized configuration) Note that the diameter of the distal end 60 of the graft 52 is smaller than the diameter of the proximal end 62 to conform to the anatomical diameter differences of the carotid arteries. This difference can be achieved by a smaller or tapered graft and stent or merely by the restriction of the vessel wall providing a counterforce against the stent.

FIG. 10 shows an alternate embodiment of a covered branch stent positioned in the external carotid artery. The branch stent 100 has petals 106 similar in configuration and function to the petals of branch stent 80 of FIG. 4 but has a smooth proximal flanged end (shown in phantom) similar to branch stent 90 of FIG. 7. It should be appreciated that a branch stent having petals only at its proximal flanged end and a smooth surface at its distal end can also be utilized. Likewise, the main stent can have optionally have petals on the distal end, proximal end or both the distal and proximal ends. The petals preferably flare out so they have a greater diameter than the other graft portions to ensure contact with the vessel wall if the vessel wall dilates. Various configurations of the petals are contemplated such as providing a narrowed waist portion and length greater than the waist portion.

FIG. 11 illustrates the main covered stent 70 of FIG. 3 implanted in the left common and internal carotid arteries. This covered stent 70 can be utilized with any of the aforedescribed covered branch stents.

FIGS. 12–14 illustrate three versions of the stent and associated graft of the present invention. Only a portion of the stent and graft are shown for convenience, it being understood that the stent and graft will have a sidewall opening, the graft can optionally have petals at the proximal and/or distal end, etc. as in the covered stents described in the aforementioned embodiments.

FIGS. 13A and 13B reflect the covered stent configuration described in the FIGS. 1–11 above, but has been provided with new reference numerals for convenience. Covered stent 200 of FIG. 13 has an outer graft material or layer 202 and inner stent 204. When stent 204 is expanded, outer graft layer 202 is compressed between the inner stent 204 and the vessel wall.

In FIGS. 12A and 12B, a stent 210 has a graft material or layer 212 on the inside of the stent 214 as shown. The graft material can be attached to stent 210, for example, by adhesive, over molding or suture. When stent 210 expands, the attached graft material (layer) is carried by the overlying stent 214 to an expanded condition. The stent 214 is therefore positioned between the graft 212 and the vessel wall and does not come in contact with the blood. The blood contacts the underlying graft material 212.

In FIGS. 14A and 14B, the covered stent 220 has two layers of graft material, namely outer layer 222 and inner layer 224. The stent 226 can either be embedded in the graft material layers or attached by various methods such as adhesive, over molding or suture. When expanded, the outer layer 222 will be sandwiched between the expanded stent 226 and the vessel wall and the inner layer 224 will contact the blood and prevent blood contact with stent 226.

Figure 15:
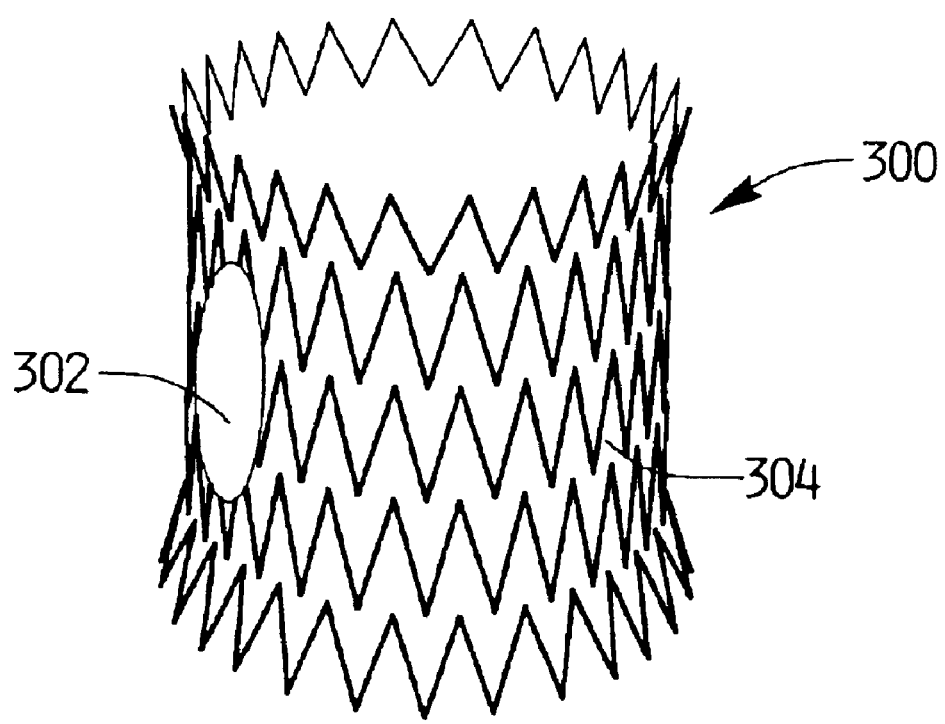
FIG. 15 is a perspective view of a stent of the present invention having an enlarged sidewall opening to accommodate blood flow from a branching vessel.

FIG. 15 illustrates a stent 300 having a side opening 302 in an intermediate portion. This illustration is provided to show the positioning of an opening in the stent as described above which would align with the respective opening in the graft of the above-described embodiments to enable insertion of a branch stent and maintenance of blood flow through the branching vessel.

FIGS. 16 and 17 illustrate an alternate configuration for treating bifurcated vessels. A pair of coil spring style stents 602, 612, each having a large diameter region 603, 613 and a smaller diameter region 605, 615 are intertwined to form a coil 600. The distal end of the larger diameter regions terminates at the juncture of the branching vessel, with the smaller diameter region 605 extending into the main vessel "x" and the smaller diameter region 615 extending into the branching vessel "y". If desired the coils 602, 612 can be used with graft material. In this case, both smaller diameter regions 605, 615 would include graft material, but only one of the larger diameter regions 603, 613 would have graft material to expose the other coiled region to enable these larger diameter regions to intermesh to secure the coils 602, 612 together.

FIGS. 18–20 illustrate several different tube like stents for treating bifurcated vessels. These bifurcated stents, shown in their expanded configuration, are preferably formed from a tube which is cut, e.g. laser cut, to the configuration shown. One advantage of these bifurcated stents of FIGS. 18–20 is that they do not change in axial length when they are compressed for insertion or change in axial length when expanded for placement in the vessel. The bifurcation is shown only in FIG. 18, it being understood that the embodiments of FIGS. 19 and 20 are similarly bifurcated.

In the first embodiment of the tubular stents, shown in FIG. 18, stent 700 is cut to form a main portion 708 and a bifurcated portion 707 extending distally from intermediate region 705 and at an angle to main portion 708. Stent 700 is shown in the expanded configuration. Stent 700 is cut to form a longitudinally extending spine 702 on bifurcated portion 707 and main portion 708 with a series of radial ribs or loops 704 terminating at tips 706. Each of the radial ribs 704 forms a C-shape with the opposing tips or tangs 706 terminating opposite one another. When compressed, each tip 706 overrides the opposing tip. Additionally, as shown, the tips 706 of ribs 704 of bifurcated portion 707 interleave with tips 706 of ribs 704 of main portion 708 to reduce the cross-sectional area in the collapsed configuration to aid insertion. Thus, the ratio between the unexpanded delivery configuration and the expanded configuration is improved.

In the embodiment of FIG. 19, the radial ribs 904, extending from linear spine 902, are offset as shown so the opposing adjacent tips 906 interleave, resulting in a smaller cross-sectional area, i.e. smaller diameter, to facilitate insertion. Only a portion of the main portion of the stent is shown, since the remaining main portion, as well as the bifurcated portion, follows the same spine/rib pattern.

In the embodiment of FIGS. 20A and 20B, increased uniform rigidity of the tube-like stent 800 is achieved by alternating the radial position of the spine rather than the continuous linear configuration of spine 702 or 902 of stents 700 or 900. FIG. 20B illustrates a segment of the stent 800 (in the expanded configuration) to show the staggering of spine 802. The remaining portion of the stent 800 follows the same staggered spine/rib configuration and stent 800 is bifurcated (not shown), i.e. a portion extends distally at an angle to the main portion, in the same manner as tube-like stents 700, 900 to accommodate bifurcated vessels. A transition portion similar to the configuration of FIG. 18 can optionally be formed in an intermediate region to help form the bifurcation. As can be seen, the spine 802 has longitudinally extending segments, for example segments 802a, 802b, 802c, that are spaced both radially and axially. Bifurcated stent 800 is consequently not only less flexible then stents 700 and 900 but also is symmetrically (uniformly) flexible in that it will have the same degree of flexibility in all orientations. Tips 806 of ribs 804 will overlap when stent 800 is compressed in a similar manner as tip 706 of stent 700. Portions of the stents 700, 800, and 900 of FIGS. 18–20, if desired, can be used with graft material.

FIGS. 21A and 21B illustrate another embodiment of a bifurcated stent, in the form of a spring like element 650 with a supporting spine 652. The spine 652 is axially and radially staggered similar to the spine of FIG. 20. However, the stent has a helical spring configuration which will elongate when radially compressed and reduce in length when expanded. Stent 650 is shown in a compressed configuration with adjacent tips or tangs 656 interleaving in a similar fashion as will tips 906 of stent 900. Only a portion of the stent 650 is shown, it being understood that the remainder of the main portion as well as the bifurcated portion of the stent (which extends at an angle like the bifurcation of the stent of FIG. 18) will have the same spine/rib pattern. A transition portion similar to the configuration of FIG. 18 can optionally be formed in an intermediate region to help form the bifurcation. Stent 650 can be laser cut from a tube. Portions of the stent 650 can be provided with graft material.

ALTERNATE APPROACHES

FIG. 22 is a perspective view of an alternative approach to accommodate a branching vessel which utilizes, a pair of juxtaposed covered stents with angled adjacent ends to accommodate blood flow from a branching vessel. This is a different approach than the aforedescribed approaches which involve implantation and utilization of a stent, either covered or uncovered, having an integral or independently attachable branch extending from the main portion. In the previous approaches, the main portion was placed in one vessel and the branch extended into a branching vessel to provide fluid communication with the main vessel and branching vessels.

In the approach of FIG. 22, a pair of covered stents 400, 410 each having angled ends 402, 412 is provided to prevent blocking off the branching vessel. Covered stent 400 is placed adjacent the juncture of the branching vessel, e.g. the common carotid artery "a", at the upstream end. Covered stent 410 is also placed adjacent the juncture, but extends downstream of the juncture, e.g. into the internal carotid artery "b". The covered stents 400, 410 preferably abut at edges 404, 414, with angled ends 402, 412 extending towards the branching vessel, thereby creating an opening for the passage of blood to the branching vessel, e.g. the external carotid artery "c." The angle preferably ranges from about 30 degrees to about 60 degrees, although other angles to accommodate blood flow are also contemplated. Also, by angling the ends of these covered or uncovered stents, intraluminal access to the branching vessel is enabled. It is also contemplated that a single covered or uncovered stent can be utilized, placed upstream of the juncture, e.g. in the common carotid artery "a", as shown in FIG. 23, so the angled end 504 of covered stent 500 will enable blood flow into the branching vessel, e.g. the external carotid artery "c".

As can also be appreciated, even though covered stents 400, 410, 500 are shown with underlying stents 406, 416, 516 and overlying graft material 408, 418, 518 respectively, the covered stents can alternatively have the graft material on the inside or both the outside or inside as described above with the other covered stent embodiments.

In yet another approach, stent 300 of FIG. 15 can be used without a graft material and placed in the vessel such that the opening 302 aligns with the lumen (passageway) in the branching vessel. If an uncovered stent is placed at the juncture of a branching vessel, although blood flow will not be completely closed off, it will be restricted because the blood will need to flow through the links or wires of the stent. Such uncovered stents would also limit future access to the branching vessel, as described above, because intraluminal access would be restricted by the links or wires. The opening 302 in stent 300 overcomes these problems. For example, stent 300 can be placed in the common carotid artery, extending into the internal carotid artery, across the juncture of the external carotid artery. The opening 302 can be aligned with the external carotid artery to allow unobstructed flow between the common carotid and external carotid arteries. This may also reduce the buildup of thrombotic material which might otherwise occur if the blood flowed through the wire mesh 304 into the external carotid artery.

Stent 300 can also be utilized in another approach wherein it has a graft material, either on the inside, outside, or both the inside and outside as described above, and is implanted without a branch portion or branch stent. For example, the stent would extend from the common carotid artery into the internal carotid artery. The opening 302 would align with the opening in the graft material and allow fluid communication with the branching vessel, e.g. the external carotid artery, as well as intraluminal access to the branching vessel.

While the above description contains many specifics, those specifics should not be construed as limitations on the scope of the disclosure, but merely as exemplifications of preferred embodiments thereof. For example, although use of a single stent is described for the main graft portion, it is also contemplated that more than one stent can be utilized to retain the main graft portion. Additionally, optionally multiple layers of graft material can be placed on the inside, outside or both the inside and outside of the stent. Also, the foregoing covered and uncovered stents of the present invention were described for use in carotid arteries, however as noted above, it is clearly contemplated that these covered and uncovered stents can be utilized in other vessels such as the coronary arteries, the descending aorta and renal arteries, the external iliac and internal iliac arteries and the common femoral and deep femoral arteries. Those skilled in the art will envision many other possible variations that are within the scope and spirit of the disclosure as defined by the claims appended hereto.

What is claimed is:

1. A system for treating stenosis in a blood vessel comprising:
   a first expandable stent and a first graft overlying the first expandable stent, the first graft having a first lumen for blood flow and having a first end, a second end, an intermediate portion between the first and second ends, and an opening in the intermediate portion;
   a second expandable stent and a second graft overlying the second expandable stent, the second graft extending at an angle to the first graft and having a second lumen communicating with the first lumen of the first graft, at least a portion of the second graft extending through the opening in the intermediate portion of the first graft
   wherein the first stent has a longitudinally extending spine and axially spaced circumferentially extending ribs extending from the spine and the second stent has a longitudinally extending spine and axially spaced circumferentially extending ribs extending from the spine, the ribs of the first stent terminate in spaced apart end portions and the ribs of the second stent terminate in spaced apart end portions, the end portions of the ribs of the first stent interleaving with the end portions of the ribs of the second stent to aid insertion.

2. The system of claim 1, wherein the longitudinally extending spine has a plurality of radially and axially spaced segments.

3. The system of claim 1, wherein the first and second stents are formed from a laser cut tube.

4. The system of claim 3, wherein adjacent ribs of the first stent are spaced apart to form gaps to receive a portion of ribs of the second stent.

5. The system of claim 1, wherein the circumferential ribs are C-shaped and each include an end portion, the end portions of ribs that are opposite one another are offset with respect to each other to enable interleaving.

6. A system for treating stenosis in a target blood vessel comprising:
   a graft portion having a main portion and a branch portion extending therefrom, the main portion having a first end, a second end and an intermediate portion between the first and second ends, the branch portion extending from the intermediate portion at an angle thereto and in fluid communication with the main portion;
   a first stent associated with the main portion and expandable from a first configuration to a second configuration to retain the main portion in position within the target vessel; and
   a second stent associated with the branch portion and expandable from a first configuration to a second configuration to retain the branch portion in position within a branching vessel wherein the branch portion is integral with the main portion;
   wherein the first stent has a plurality of ribs having first end portions and the second stent has a plurality of ribs having second end portions, wherein the first end portions interleave with the second end portions to reduce the cross sectional area for insertion.

7. The system of claim 6, wherein the first and second stents are positioned within the main and branch portions, respectively, so the main and branch portions expand upon expansion of their respective stents.

8. The system of claim 6, wherein the main and branch portions each include a longitudinally extending spine.

9. The system of claim 6, wherein the main and branch portions include a series of spines spaced axially and radially with respect to each other.

10. The system of claim 6, wherein the first and second stents are formed from a laser cut tube.

11. A system for treating stenosis in a target blood vessel comprising:
    a graft having a first end portion, a main portion and a second end portion, the second end portion being bifurcated to form a main portion extension and a branch portion, the branch portion and the main portion extension being in fluid communication;
    a first stent positioned within at least the main portion or the first end portion and expandable from a first configuration to a second configuration to retain the graft in position within the target vessel wherein the first stent has a longitudinally extending spine and axially spaced circumferentially extending ribs extending from the spine; and
    a second stent positioned in the branch portion and expandable from a first configuration to a second configuration to retain the branch portion in position within a branching vessel;
    wherein each of the ribs forms a C-shape with opposing end portions terminating opposite one another and spaced apart from one another.

12. The system of claim 11, wherein the first and second stents are formed from a laser cut tube.

13. The system of claim 11, wherein the second stent includes a plurality of curved ribs each having first and second end portions, the end portions of the ribs of the, first stent are offset with respect to the end portions of the ribs of the second stent.

14. The system of claim 13, wherein end portions of the ribs of the first stent interleave with end portions of ribs of the second stent.

* * * * *